United States Patent [19]

Bowen

[11] Patent Number: 4,588,756
[45] Date of Patent: May 13, 1986

[54] MULTI-STEP METHOD FOR OBTAINING STRONG ADHESIVE BONDING OF COMPOSITES TO DENTIN, ENAMEL AND OTHER SUBSTRATES

[75] Inventor: Rafael L. Bowen, Gaithersburg, Md.

[73] Assignee: American Dental Association Health Foundation, Washington, D.C.

[21] Appl. No.: 699,079

[22] Filed: Feb. 7, 1985

Related U.S. Application Data

[63] Continuation-in-part of Ser. No. 516,956, Jul. 25, 1983, Pat. No. 4,521,550, which is a continuation-in-part of Ser. No. 457,029, Jan. 10, 1983, Pat. No. 4,514,527.

[51] Int. Cl.$^4$ .............................................. A61K 6/00
[52] U.S. Cl. .............................. 523/116; 260/998.11; 106/35; 523/114; 523/115; 424/147; 433/228.1
[58] Field of Search .................... 433/228; 260/998.11; 106/35; 523/114, 115, 116; 424/147, 295

[56] References Cited

U.S. PATENT DOCUMENTS

| | | | |
|---|---|---|---|
| 3,200,142 | 8/1965 | Bowen | 106/35 |
| 3,635,889 | 1/1972 | Bowen | 106/35 |
| 3,785,832 | 1/1974 | Bowen | 106/35 |
| 4,148,988 | 4/1979 | Masuhara et al. | 106/35 |
| 4,251,565 | 2/1981 | Bowen | 433/226 |

FOREIGN PATENT DOCUMENTS

1448134  9/1976  United Kingdom .................. 106/35

OTHER PUBLICATIONS

Bowen, R. L., "Adhesive Bonding of Various Materials to Hard Tooth Tissues, XXII, The Effects of a Cleanser Mordant, & PolySAC on Adhesion Between a Composite Resin and Dentin," 59, *J. Dent. Res.*, 809–814 (1980).
Bowen, R. L., "Adhesive Bonding of Various Materials to Hard Tooth Tissues, XIX, Solubility of Dentinal Smear Layer in Dilute Acid Buffers," 28, *Int'l Dent. J.*, 97–104 (1978).
Bowen, R. L., "Adhesive Bonding of Various Materials to Hard Tooth Tissues, VII, Metal Salts as Modants for Coupling Agents," in Moskowitz, H.; Ward, G.; & Woolridge, E., (Eds.); *Dental Adhesive Materials*, 205–221, Proceedings from Symposium held Nov. 8–9, 1973 at the Hunter–Bellevue School for Nursing, New York City, Presitge Graphic Services.
Bowen, R. L., "Adhesive Bonding of Various Materials to Hard Tooth Tissues, II, Bonding to Dentin Promoted by a Surface-Active Comonomer," 44, *J. Dent. Res.*, 895–902 (1965).
Bowen, R. L., "Adhesive Bonding of Various Materials to Hard Tooth Tissues, III, Bonding to Dentin Improved by Pretreatment and the Use of a Surface Active Comonomer," 44, *J. Dent. Res.*, 903–905 (1965).
Bowen, R. L., "Adhesive Bonding of Various Materials to Hard Tooth Tissues, IV, Bonding to Dentin, Enamel, and Fluorapatite Improved by the Use of a Surface-Active Comonomer," 44, *J. Dent. Res.*, 906–911 (1965).
Bowen, R. L., "Adhesive Bonding of Various Materials to Hard Tooth Tissues, V, The Effect of a Surface-Active Comonomer on Adhesion to Diverse Substrates," 44, *J. Dent. Res.*, 1369–1373 (1965).
Plueddemann, E., *Interfaces in Polymer Matrix Composites*, 200 (1974).
Jedrychowski, et al., "Influence of a Ferric Chloride Mordant Solution on Resin–Dentin Retention," 60, *J. Dent. Res.*, 134–138 (1981).
Sax, N. I., *Dangerous Properties of Industrial Materials*, 715 (1957).
Dwyer, F. & Mellor, D., *Chelating Agents and Metal Chelates*, 311 (1964).
Sneed, M. & Maynard, J., *General Inorganic Chemistry*, 1080 (1942).
Bowen, R. L., "Adhesive Bonding of Various Materials to Hard Tooth Tissues, I, Method of Determining Bond Strength," 44, *J. Dent. Res.*, 690–695 (1965).
Bowen, R. L., "Investigation of the Surfaces of Hard Tooth Tissues by a Surface Activity Test," in Phillips, R., & Ryge, G. (Eds.): *Proceedings of the Workshop on Adhesive Restorative Dental Materials*, 177–191, at Indiana University, Sep. 28–29, 1961, Spencer, Indiana: Owen Litho Service.
Bowen, R. L., "Development of an Adhesive Restorative Material," in *Adhesive Restorative Dental Materials II*, 225–231, Univ. of Virginia Workshop, Public Health Service Publication No. 1494, (Washington, D.C.: U.S. Government Printing Office, 1966).

(List continued on next page.)

*Primary Examiner*—Ronald W. Griffin
*Attorney, Agent, or Firm*—Allegretti, Newitt, Witcoff & McAndrews, Ltd.

[57] ABSTRACT

Materials and methods for improving the adhesion of composite materials and resins to dentin, enamel and other substrates are disclosed. Preferably, the substrate surface is treated with an aqueous solution of (1) at least one acidic salt containing a polyvalent cation which preferably is capable of changing valence by unit steps (univalent changes) and which can bind to dentin or enamel surface sites, and at least one anion which preferably forms a relatively water-insoluble precipitate or precipitates with calcium, and which contains at least one carboxyl group and preferably two or more carboxyl groups; and (2) acid, preferably nitric acid. The resultant surface is then treated with a solvent containing at least one compound selected from the group consisting of (1) N-phenylglycine, (2) the adduct of N (p-tolyl) glycine and glycidyl methacrylate, and (3) the addition reaction product of N-phenylglycine and glycidyl methacrylate. Finally, a solution is applied which contains at least one compound selected from the group consisting of (1) the addition reaction product of pyromellitic acid dianhydride and 2-hydroxyethyl methacrylate ("PMDM"), (2) the addition reaction product of 3,3',4,4'-benzophenonetetracarboxylic dianhydride and 2-hydroxyethyl methacrylate ("BTDA-HEMA"), and (3) 4-methacryloxyethyltrimellitic anhydride ("4-META"). Alternative embodiments are also set forth.

32 Claims, No Drawings

OTHER PUBLICATIONS

Lal, et al., "New Polymerization Catalysts for Methyl Methacrylate," 24, *J. Polym. Sci.*, 75–84 (1957).

Uehara, "Polymerization of Methyl Methacrylate Initiated by a Combined Action of Trichloroacetic Acid and Dimethylaniline," 31, *Bull. Chem. Soc. Jap.*, 685–687 (1958).

Hrabak, et al., "The Initiation of Polymerization of Unsaturated Tertiary Amines with Carboxylic Acids," 182, *Macromol. Chem.*, 1595–1603 (1981).

Palit, S. R. and Koner, R. S., "Permanganate-Oxalic Acid as a Redox Initiator in Aqueous Media," 57, *J. Polymer Sci.*, 609–615 (1962).

Bowen, R. L.; Cobb, E. N.; and Rapson, J. E., "Adhesive Bonding of Various Materials to Hard Tooth Tissues: Improvement in Bond Strength to Dentin", *J. Dent. Res.*, 61 (9): 1070–1076, Sep., 1982.

Bowen, R. L. and Cobb, E. N., "A Method for Bonding to Dentin and Enamel", *JADA*, vol. 107, Nov., 1983.

4,588,756

MULTI-STEP METHOD FOR OBTAINING STRONG ADHESIVE BONDING OF COMPOSITES TO DENTIN, ENAMEL AND OTHER SUBSTRATES

This invention was supported in part by USPHS Research grant DE-05129 to the American Dental Association Health Foundation from the National Institute of Dental Research, Bethesda, Md.

BACKGROUND OF THE INVENTION

1. Field Of The Invention

This application is a continuation-in-part of co-pending application Ser. No. 516,956, filed July 25, 1983, now U.S. Pat. No. 4,521,550, issued June 4, 1985, which is in turn a continuation-in-part of co-pending application Ser. No. 457,029 filed Jan. 10, 1983 now U.S. Pat. No. 4,514,527, issued Apr. 30, 1985.

This invention relates to methods of improving adhesive bonding of acrylic resins to industrial and dental substrates, and more particularly to dental restoration methods and methods of improving adhesion of composite dental materials to dentin and enamel. More specifically, methods for durable adhesive bonding of composite resins to dentin are disclosed with the objects of improving treatment of cervical erosions, root caries, and other dental conditions and of eliminating much mechanical cutting of dentin now required for retention of restorations.

2. Description Of The Prior Art

For many years, advances in the study of methods of adhesive bonding of composite materials to hard tooth tissues have evolved by small increments. Previous experiments in adhesive bonding of composite materials to dentin demonstrated beneficial effects from cleansers, mordants, and adhesion promoting coupling agents; see, for example, Bowen, R. L., "Adhesive Bonding of Various Materials to Hard Tooth Tissues. XXII. The Effect of a Cleanser Mordant, and PolySAC on Adhesion Between a Composite Resin and Dentin," 59 *J. Dent. Res.* 809–814 (1980); Bowen, R. L., "Use of Polyfunctional Surface-Active Comonomer and Other Agents to Improve Adhesion Between a Resin or Composite Material and a Substrate," U.S. Pat. No. 4,251,565, February 1981; Bowen, R. L., "Adhesive Bonding of Various Materials to Hard Tooth Tissues. XIX. Solubility of Dentinal Smear Layer in Dilute Acid Buffers," 28 *Int'l Dent. J.* 97–104 (1978); Bowen, R. L., "Adhesive Bonding of Various Materials to Hard Tooth Tissues. VII. Metal Salts as Mordants for Coupling Agents," in Moskowitz, H.; Ward, G.; & Woolridge, E., (eds.); *Dental Adhesive Materials* 205–221, Proceedings from Symposium held Nov. 8–9, 1973 at the Hunter-Bellevue School for Nursing, New York City, Prestige Graphic Services (1974).

The rationale for using a surface-active comonomer as a coupling agent to improve bonding has been supported by previous data. Bowen, R. L., "Adhesive Bonding of Various Materials to Hard Tooth Tissues. II. Bonding to Dentin Promoted by a Surface-Active Comonomer," 44 *J. Dent. Res.* 895–902 (1965); Bowen, R. L., "Adhesive Bonding of Various Materials to Hard Tooth Tissues. III. Bonding to Dentin Improved by Pretreatment and the Use of a Surface-Active Comonomer," 44 *J. Dent. Res.* 903–905 (1965); Bowen, R. L., "Adhesion Bonding of Various Materials to Hard Tooth Tissues. IV. Bonding to Dentin, Enamel, and Fluorapatite Improved by the Use of a Surface-Active Comonomer," 44 *J. Dent. Res.* 906–911 (1965); Bowen, R. L., "Adhesive Bonding of Various Materials to Hard Tooth Tissues. V. The Effect of a Surface-Active Comonomer on Adhesion to Diverse Substrates," 44 *J. Dent. Res.* 1369–1373 (1965). The addition reaction product of N-phenylglycine and glycidyl methacrylate (NPG-GMA) and the addition reaction product of N-phenylglycine and p-chlorophenyl glycidyl ether (NPG-CGE) are disclosed, respectively, as vehicles to improve adhesive bonding to a limited extent in Bowen, U.S. Pat. No. 3,200,142, Aug. 10, 1965, and in Bowen, British Pat. No. 1,448,134 and U.S. Pat. No. 3,785,832, Jan. 15, 1974.

Although an acid-etch technique has been effective in beneficiating the bonding of composite and unfilled resins to enamel of teeth, no method has existed for achieving strong adhesive bonding between composite and unfilled resins and dentin. Many investigators have been attempting to achieve significantly enhanced adhesive bonds to both dentin and enamel and various other substrates for well over twenty-five years without adequate success.

SUMMARY OF THE INVENTION

The present invention comprises materials and methods which appreciably increase the previously obtainable strengths of adhesive bonds between composite materials or resins and dentin in vitro, and also result in effective bonding between these materials or resins and enamel and other substrates. Thus, it is an advantage of this invention to provide materials and methods for improved adhesive bonding of composite and unfilled resins of the type polymerized by free radicals to dentin, enamel, industrial substrates, and/or other substrates containing or capable of binding metallic ions (i.e., ions of elements on the left side and in the center of the periodic table). The resulting products are also within the scope of the invention.

Briefly, the method of the invention is preferably accomplished by treating the surface of dentin or enamel with an aqueous solution (or solutions) of (1) at least one acidic salt containing a polyvalent cation which preferably is capable of changing valence by unit steps (univalent changes) and which can bind to dentin or enamel surface sites, and at least one anion which preferably forms a relatively water-insoluble precipitate or precipitates with calcium, and which contains at least one carboxyl group and preferably two or more carboxyl groups; and (2) acid. The resultant surface is then treated with a solvent containing at least one compound selected from the group consisting of (1) N-phenylglycine (NPG), (2) the adduct of N(p-tolyl)glycine and glycidyl methacrylate ("NTG-GMA"), and (3) the addition reaction product of N-phenylglycine and glycidyl methacrylate ("NPG-GMA"). Finally, a solution is applied which contains at least one compound selected from the group consisting of (1) the addition reaction product of pyromellitic acid dianhydride and 2-hydroxyethyl methacrylate ("PMDM"), (2) the addition reaction product of 3,3',4,4'-benzophenonetetracarboxylic dianhydride and 2-hydroxyethyl methacrylate ("BTDA-HEMA"), and (3) 4-methacryloxyethyltrimellitic anhydride ("4-META"). Alternatively, but less preferred, the contacting with PMDM, BTDA-HEMA and/or 4-META solution may precede the contacting with the NPG, NTG-GMA and/or NPG-GMA solution. The order of application of these materials may be otherwise varied, and in some instances application of certain of the materials may be omitted. The components for practicing the method of the invention may be conveniently made available in the form of a kit or article of manufacture.

In a highly preferred embodiment of the invention, it has recently been discovered that the presence of nitric acid in the first aqueous treatment solution in combination with ferric oxalate results in a relative improvement in bond strengths for the bonding of composite materials and resins to dentin and enamel. An aqueous solution of ferric oxalate and nitric acid is contacted with the surface of the dentin or enamel, after which the surface is washed and dried. Subsequent to washing and drying the surface, a solution of NPG, NTG-GMA and/or NPG-GMA in acetone is contacted with the surface. Any excess of the NPG, NTG-GMA or NPG-GMA is removed by the application of clean acetone which is then removed before it evaporates, and the surface is dried. An acetone solution of PMDM, BTDA-HEMA and/or 4-META is then applied. Finally, the surface of the dentin or enamel is dried. The surface is then ready for application of a composite or dental resin which, upon hardening, will adhere to the substrate surface.

In a particularly preferred embodiment of the invention, NPG is employed as the primary active agent in the second treatment solution of the above method. One advantage of NPG is that it is widely commercially available. It is used commercially in the preparation of synthetic indigo blue, which is employed for dyeing denims. Another advantage of NPG is that it is not vulnerable to premature polymerization during synthesis or storage, either pure or in solutions, because it does not contain monomeric moieties (methacrylate groups).

Alternatively, the method of the invention is accomplished by treating the surface of the dentin, enamel or other substrate containing or capable of binding metallic ions with a solution which contains (1) at least one salt of a polyvalent cation which is preferably capable of changing valence by unit steps and which can bind to substrate surface sites, and an anion which contains at least one carboxyl group and preferably two or more carboxyl groups; and (2) acid. The resultant substrate surface is then treated with a material or a solvent containing at least one surface-active compound selected from the group consisting of (1) NPG, (2) NTG-GMA, (3) NPG-GMA, and (4) other compounds each of which contain at least one of each of the following groups: carboxyl and amino. The surface active compound may be a surface active comonomer which contains a moiety capable of free radical polymerization as well as the carboxyl and amino groups. Finally, a material or solution is applied which contains at least one compound selected from the group consisting of (1) PMDM and/or BTDA-HEMA, (2) 4-META, and (3) other compounds containing at least one group or moiety capable of free radical polymerization, and at least one aromatic ring or moiety containing electron-withdrawing substituents which do not interfere with free radical polymerization, and which compound preferably also contains one or more free carboxyl groups, or anhydride groups which can form free carboxylic groups upon hydrolysis.

DESCRIPTION OF PREFERRED EMBODIMENTS

The Most Preferred Embodiments Of The Invention

This aspect of the invention comprises materials and methods for improving the adhesion of composite materials to dentin and enamel. The invention also comprises the resultant products. The terms "composite material" and "composite resin" are used herein to refer to materials which can polymerize or harden by a free radical mechanism. Typical examples include methacrylates, acrylates, and polyesters.

The most preferred inventive method for preparing the surface of dentin and enamel for adhesion of composite materials comprises contacting the surface of dentin or enamel with an aqueous solution of (1) at least one acidic salt containing a polyvalent cation which can change valence by unit steps and an anion which preferably forms a relatively water-insoluble precipitate with calcium and which contains at least one carboxyl group and preferably two or more carboxyl groups; and (2) acid. This process deviates fundamentally from prior art two-step procedures of (1) cleansing to remove the smeared surface layer on the dentin or enamel, and (2) "mordanting" to improve bonding sites for later-applied adhesive agents.

The anion of the acidic salt forms an insoluble precipitate with calcium, and/or remains or becomes complexed with the cation of the acidic salt during interaction with the substrate surface. The cation also becomes bound to or part of the substrate surface. In preferred acidic salt species, the cation can also form a relatively insoluble phosphate. As a result, if these reaction products were to solidify among collagenous strands which were uncovered by the dissolution of the apatite in the surface dentin, a restructured surface layer might be formed that would be microporous, physically rigid, and chemically receptive to adhesive agents and composite resins. Water-soluble residues are preferably avoided on the theory that water-soluble substances in adhesive joints might, upon imbibition of water, become osmotically active and develop pressures that tend to push apart the bonded materials. See Plueddemann, E., *Interfaces in Polymer Matrix Composites* 200 (1974). Thus, mordants such as ferric chloride, although they increase adhesive bond strengths (See Bowen, R. L., "Adhesive Bonding of Various Materials to Hard Tooth Tissues. XXII. The Effects of a Cleanser, Mordant and PolySAC on Adhesion Between a Composite Resin and Dentin," 59 *J. Dent. Res.* 809–814 (1980); Jedrychowski, et al., "Influence of a Ferric Chloride Mordant Solution on Resin-Dentin Retention," 60 *J. Dent. Res.* 134–138 (1981)), might leave behind soluble calcium chloride that would have a weakening effect on the bonds.

The most preferred acidic salt containing a polyvalent cation which can change valence by unit steps and containing an anion which forms a relatively insoluble precipitate with calcium and which has carboxyl groups is ferric oxalate. Ferric oxalate is water-soluble, yields a low pH, contains a cation that forms relatively insoluble phosphates (at physiological pH), and can reversibly change valence from 3 to 2. Ferric oxalate also contains an anion that has two carboxyl groups and forms insoluble calcium compounds. Ferric oxalate is of only slight toxicity unless ingested in quantity. See Sacks, N. I. *Dangerous Properties of Industrial Materials* 715 (1957).

The most preferred concentration of the aqueous ferric oxalate solution is 5.3% anhydrous iron (III) oxalate (6.8% of the hexahydrate, $Fe_2(C_2O_4)_3 \cdot 6H_2O$). Higher and lower concentrations, preferably within the range of about 0.1% to a saturated solution, may be used, but give slightly less enhancement of the strength of the bond between composite and dentin. A 4% solution of ferric oxalate, which is an isotonic concentration (4% $Fe_2(C_2O_4)_3 \cdot 6H_2O$, 290 mOsm, pH 1.01) gives reasonable results and might be associated with better pulp response as a result of the physiological activity of its water content.

The acid which is also preferably present in the first treatment solution renders the solution low in pH. The most preferred acid for use in the inventive method is nitric acid, ranging in concentration from 0 to 50% by weight, preferably 0.068 to 10% by weight and most preferably of a concentration of about 2.5% by weight of the aqueous solution. It has been discovered that commercially available ferric oxalate may contain a minor amount of nitric acid, on the order of 0.068 to 0.68% in some instances, so that nitric acid may be provided by a commercially supplied solution of ferric oxalate in and of itself. It is believed that acids other than nitric, for example, phosphoric acid, hydrochloric acid, sulfuric acid and others, may similarly be effective in improving the bond strengths obtainable in the use of the present invention. While the acid is preferably present with the ferric oxalate (or other salt) in a single first treatment solution, the acid and salt may alternatively be applied in separate steps from separate solutions, e.g., application of a solution of nitric acid followed by application of a solution of ferric oxalate.

After application of the aqueous solution of (1) an acidic salt containing a polyvalent cation that can change valence by unit steps, and an anion with carboxyl groups which preferably forms a relatively insoluble precipitate with calcium; and (2) acid; the surface of the dentin or enamel is washed, generally with water, and blown dry, ordinarily with air. Nitrogen, although usually not as readily available as air, is at least as good as a drying agent for this purpose.

As the next step in the most preferred inventive method, a solution of NPG or of NTG-GMA in a volatile, water-miscible solvent is applied to the surface of the dentin or enamel.

NPG is available commercially. It can be synthesized by the route of Example 1b with the exception that analine is substituted for p-toluidine. NPG is of the following formula:

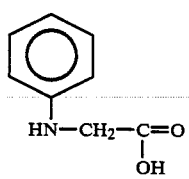

NPG

NTG-GMA is the adduct of N(p-tolyl)glycine and glycidyl methacrylate, and is of the following formula:

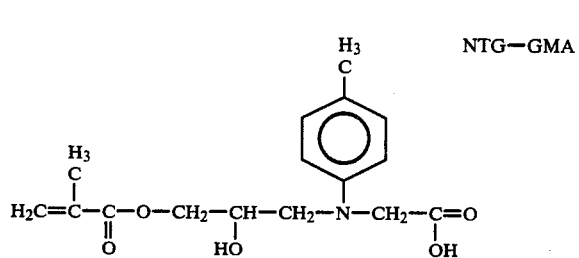

NTG-GMA

NTG-GMA may be synthesized readily from commercially available compounds by the route of Example 1b. NTG-GMA has been found to be superior to NPG-GMA in the bond strengths obtainable by the method of the present invention.

NPG or NTG-GMA can be applied to dentin and enamel surfaces dissolved in a volatile water-miscible solvent. In this context, the term "solvent" is intended to include solvent mixtures. The preferred solvent is acetone, which is miscible with water (thereby allowing water-insoluble solutes like NPG or NTG-GMA to make intimate approach to substrate surface sites), volatile, and relatively innocuous; it may also have other advantageous characteristics. A 10% solution of NPG or NTG-GMA in acetone is efficacious. Other concentrations, preferably within the range of about 0.1% to a saturated solution, and other solvents, singly and as mixtures, may be employed. Isopropyl alcohol (2-propanol) is not recommended as a solvent because it resulted in tooth-to-resin bond strengths less than one-half those achieved when acetone was used.

After the solution of NPG or NTG-GMA has remained in place preferably about 30 to about 90 seconds, 60 seconds being most preferred, excess solvent is removed if the solution has not evaporated to dryness; the surface of the dentin or enamel is then wetted with clean solvent, e.g., acetone; and preferably after 1 to 20 seconds, 10 seconds being most preferred, excess solvent is removed and the tooth surface is then dried, generally with air.

As the next major step in the most preferred inventive method, a solution of PMDM and/or BTDA-HEMA in the same or a different volatile solvent(s) is applied to the surface of the dentin or enamel. PMDM is the addition product of pyromellitic acid dianhydride and 2 moles of 2-hydroxyethyl methacrylate. While the structure(s) of PMDM are not definitely known, and it is best characterized as the above-recited addition reaction product, the structures of the two isomers of PMDM are postulated to be as follows:

PMDM

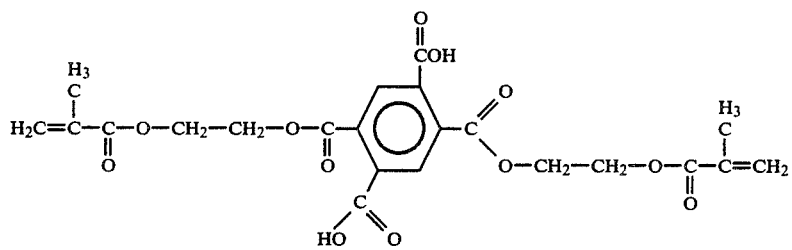

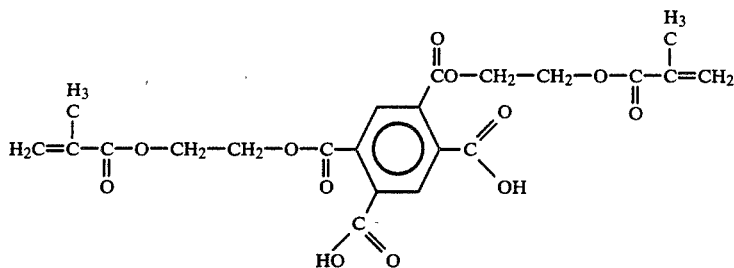

A method for the synthesis of PMDM is described in Example 1d, below. Although the isomer melting at about 163° C. gave bond strengths slightly higher than did the isomer melting at 153° C., they were both effective individually and when admixed. The PMDM isomers may be applied to the dentin or enamel surface in any desired proportions, dissolved in a solvent or a mixture of solvents. Again, the preferred solvent is acetone, although other solvents as listed below may be used. A 5% solution of PMDM in acetone is efficacious, although other concentrations, preferably in the range of about 0.1% to a saturated solution, may be used.

BTDA-HEMA is the addition reaction product of 3,3',4,4'-benzophenonetetracarboxylic dianhydride and 2 moles of 2-hydroxyethyl methacrylate, and one of its isomers is of the following formula

BTDA—HEMA

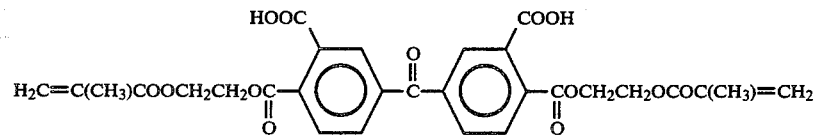

A method for the synthesis of BTDA-HEMA is also given in Example 1d.

Preferably, the excess solution of PMDM and/or BTDA-HEMA is not removed, but rather, the solvent is removed by evaporation that may be speeded by applying a gentle stream of air at any feasible temperature.

Advantageously, the components necessary to effect the method of this invention may be packaged in an article of manufacture of "kit" for use by the dentist. As an illustration for the most preferred embodiment of the invention, such an article of manufacture would comprise (a) a first closed compartment that is preferably impervious to ultra-violet and blue light (e.g., an amber glass bottle) or is impervious to ultra-violet and all visible light, containing ferric oxalate and nitric acid (and which may additionally contain other additives); (b) a second closed compartment that is also preferably impervious to ultraviolet and blue light or to all light, containing NPG or NTG-GMA; and (c) a third closed compartment that is preferably impervious to UV or visible light containing PMDM and/or BTDA-HEMA. The nitric acid would be included in the kit in solution form, and, optionally, the ferric oxalate, NPG or NTG-GMA and PMDM and/or BTDA-HEMA may be provided in the form of solutions, or in a form which will facilitate preparation of solutions.

After the dentin or enamel surface is prepared as described above, a mix of composite or unfilled resin may be applied. Many bonds to dentin or enamel of extracted teeth have required over one ton (2,000 lbs.) per square inch to break in tension, with fractures occurring occasionally within the dentin itself and frequently in the composite material, as well as at regions in between these two materials. The following example illustrates certain aspects of the above-described method and advantageous results.

EXAMPLE 1a

Preparation and Application of Ferric Oxalate/Nitric Acid Solutions

A solution of an acidic salt containing a polyvalent cation capable of changing valence by unit steps and an anion which has carboxyl groups and forms an insoluble precipitate with calcium was prepared by dissolving iron (III) oxalate, $Fe_2(C_2O_4)_3 \cdot 6H_2O$ in distilled water at a concentration of about 6.8% of the hexahydrate (5.3% anhydrous ferric oxalate). After the oxalate slowly dissolved, the solution was filtered giving a clear, yellow color with a pH of about 0.84 and an osmotic concentration of 480 mOsm. It is believed, based on the pH of this solution and the discovery that later samples of ferric oxalate from the same commercial source (Alfa Ventron Products, Danvers, Maine) contained low concentrations of nitric acid, that this solution of ferric oxalate contained 0.68% $HNO_3$. A drop of this solution was placed for 60 seconds on freshly-resurfaced dentin from an extracted human molar, then washed off with distilled water for 10 seconds. The surface was then blown dry with a compressed air stream (10 seconds). Scanning electron micrographs of cut dentin surfaces indicated that the smeared surface layer was altered by the solution, with the dentinal tubules enlarged only superficially and partially filled with reaction products.

An isotonic concentration of ferric oxalate (4% $Fe_2(C_2O_4)_3 \cdot 6H_2O$, 290 mOsm, pH 1.01) and a 2% (based on the hydrate) concentration (142 mOsm, pH 1.30) were also prepared and tested. The ferric oxalate solutions were kept in amber dropper bottles at room temperature. A 6.8% ferric oxalate solution believed to contain 0.68% nitric acid was kept in an amber dropper bottle at room temperature and used in the most preferred method intermittently for over one year with no decrease in resulting bond strengths to dentin when compared with a freshly prepared solution. However, ferric oxalate solutions do decompose in clear glass containers because of the effects of light. See Dwyer, F. & Mellor, D., *Chelating Agents and Metal Chelates* 311 (1964); Sneed, M. & Maynard, J., *General Inorganic Chemistry* 1080 (1942).

EXAMPLE 1b

Synthesis of NTG (N-p-tolylgycine)

Para-toluidine (2.43 mols) was reacted with monochloroacetic acid (2.00 mols) and sodium hydroxide (2.00 mols) in a methanol-water solution at reflux (about 80° C.) for about 5 hours. The methanol was boiled off, and the NTG (N(p-tolyl)glycine, also known as N(4-methylphenyl)glycine), precipitated on cooling from water. The excess toluidine was removed by extraction with ether, and the recrystallized NTG had a melting range that included 110° C.

Improved purity and yield would be expected if the reaction were carried out in an inert atmosphere and if antioxidants were used. There are also other synthesis routes known to those skilled in the art of organic synthesis: esters of chloroacetic acid, bromoacetic acid, and/or iodoacetic acid can be reacted with para-toluidine, and the ester groups removed subsequently by hydrolysis. For example, a solution of methyl or ethyl bromoacetic acid is added slowly with stirring to a solvent or mixture of solvents such as methanol, ethanol, water, acetone, methyl-ethyl ketone, etc., containing para-toluidine; the temperature is increased only as necessary to effect the condensation reaction at the desired rate; catalysts and/or acid scavengers, such as sodium, potassium, calcium, magnesium, or other carbonates, bicarbonates, oxides, hydroxides, etc., or molecular sieves 3A, etc., or sterically hindered tertiary amines, are added before or during the reaction to remove HCl, HBr, or HI as it is released during the condensation reaction. The resulting NTG can be purified by filtration and recrystallization from the same or other solvents if a haloacetic acid was used in the foregoing reaction. If a haloacetic acid ester was used in the foregoing reaction, NTG can be obtained by hydrolyzing the N-tolylglycine ester by boiling with aqueous base (such as a sodium hydroxide solution) or by other methods known in the art of organic chemistry.

Synthesis of NTG-GMA

An aqueous solution of the NTG, neutralized with sodium hydroxide, was stabilized with hydroquinone and di-t-butyl sulfide; to it was added, dropwise with stirring, a methanolic solution of glycidyl methacrylate (GMA) at 23° C. The reaction was slightly exothermic, reaching 33° C. Fine needles of the sodium salt of the NTG-GMA were separated by vacuum filtration. A methanol/water solution of this, containing hydroquinone as stabilizer, was acidified to a pH of about 4, whereupon the NTG-GMA precipitated as fine white needles with a melting range of about 104° to 112° C. These dried crystals were stored in a refrigerator in the dark. When the 5% acetone solutions were prepared (considerably later) for the tests reported in Table 1, some undissolved solids remained (presumably polymer that had formed during storage); the solution was filtered before use.

Alternative methods of synthesis of NTG-GMA are expected to be capable of improving the yield. For example, catalysts (guiacol, phenol, acids with a pKa higher than NTG, etc.), optimization of solvents and reaction temperatures, improved stabilizers against autoxidation and premature polymerization, especially during the acidification step (picric acid, ascorbic acid, etc.) can be used. It might be feasible to add GMA to the para-toluidine before the haloacetic acid or its salt or ester is condensed to the nitrogen atom in that product. However, these alternative synthesis pathways would be expected to yield variation in comparative percent yield, purity, convenience, economy, and the like.

EXAMPLE 1c

Application of NTG-GMA

In a series of experiments, NTG-GMA was applied to the dentin surface as an acetone solution. Nominal concentrations ranging from 1.25% to 10% were compared, and the highest concentration gave the highest bond strength. Therefore, higher concentrations (even higher than 10%) might be even more effective, within the limits of solubility. The solubility of highly purified NTG-GMA crystals may be on the order of slightly less than 10% by weight in acetone. One drop of 10% acetone solution was placed on the horizontal dentin surface and allowed to remain there for 60 seconds (the specimen was covered over with an inverted glass beaker to retard evaporation of the solvent due to the ventilation air stream in the exhaust hood). If excess solution remained, it was removed with a cotton swab, care being taken to avoid touching the part of the surface to be bonded.

A drop of pure acetone was then placed on the dentin surface for 10 seconds and then likewise removed with a cotton swab again, moving circumferentially; this acetone solvent removed excess NTG-GMA that was not chemically or physically bound to the surface. (Otherwise, NTG-GMA is prone to recrystallize on the surface due to solvent evaporation; these crystals of NTG-GMA can weaken the bonds.) The dentin surface was then dried with a compressed air stream for 10 seconds.

The NTG-GMA used in these experiments was stored under refrigeration in the dark until the current solutions were prepared. Turbidity of the acetone solution indicated that the material had polymerized somewhat during storage; the solution was filtered before use giving a clear and essentially colorless liquid when freshly prepared.

EXAMPLE 1d

Synthesis of PMDM and BTDA-HEMA

PMDM was prepared by heating together 1 mol of pyromellitic acid dianhydride and a slight excess of 2 mols of 2-hydroxyethyl methacrylate in xylene together with a small amount of the monomethyl ether of hydroquinone as a stabilizer. On cooling and standing, there was a crystalline precipitate. Fractional crystallization yielded two portions, one melting at about 153° C. (with polymerization) and the other melting at about 163° C. (with polymerization); the mixed melting point was about 146° C. These crystalline solids were stored in amber bottles in the dark at room temperature until utilized in the current experiments considerably later. The crystals were dissolved in acetone to form a slightly turbid 5% solution which retained its turbidity on filtration. The clear supernatent or a solution clarified by centrifugation was used in these experiments.

PMDM can be synthesized more readily by combining the pyromellitic acid dianhydride with 2-hydroxyethyl methacrylate in the presence of anhydrous, aprotic catalysts and anhydrous, aprotic solvents such as dimethyl formamide, dimethyl sulfoxide, diethylene glycol dimethyl ether, acetone, methylethyl ketone, tetrahydrofuran, and/or other inert or catalytic solvents in which both of these reagents are at least slightly soluble. Examples of catalytic solvents would be pyridine, triethyl amine, or other aprotic, anhydrous, tertiary aliphatic or aromatic amines. Catalysts that can be used to good advantage in the synthesis in inert solvents include N,N-dimethylamino ethyl methacrylate, N,N-diethylamino ethyl methacrylate, triethyl amine, pyridine, and other compounds that can catalytically accelerate or facilitate the reaction of an alcoholic moiety with an acid anhydride moiety. For instance, 2-hydroxyethyl methacrylate and N,N-dimethylamino ethyl methacrylate could be added to pure, dry acetone containing a trace of a polymerization inhibitor (such as MEHQ); then, with stirring, finely divided pyromellitic acid dianhydride is added, whereupon the dianhydride will dissolve, react, and form a useful solution of the desired PMDM in situ. The original quantities (concentrations) can be such as to yield the desired final concentration (e.g., 5%) of the active ingredients for use with or without further dilution. The concentration of the amine catalyst can vary from 0.1 to 68 mole percent of the theoretical yield of PMDM.

BTDA-HEMA may be synthesized by an analogous set of procedures, substituting in place of the pyromellitic acid dianhydride the following:

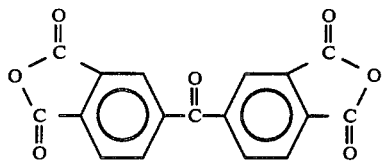

EXAMPLE 1e

Application of PMDM

One drop of a 5% acetone solution of PMDM was placed on a horizontal dentin surface and the specimen was covered with an inverted beaker; after 60 seconds, excess liquid, if any, was removed around the periphery (beyond the bonded area) with a clean cotton swab; the surface was blown with compressed air for 10 seconds to further remove solvent. The surface then had a semi-glossy appearance, due to a thin layer of PMDM which was not removed. The composite resin was then applied using conventional techniques.

EXAMPLE 1f

Application of Composite Resin and Testing of Bond Strength

After the dentin surface was prepared by the foregoing treatments of Examples 1a, 1c, and 1e in a variety of sequences as indicated below, a mix of a composite resin (for example Adaptic ® Dental Restorative, available from Johnson & Johnson, East Windsor, N.J.; Concise ® from 3M Co., St. Paul, Minn.; or others from other companies) was made, applied to the opposing plunger part of a test assembly, slowly let down onto the dentin surface, and weighted with a pressure of about 1.0 MPa (150 psi) for 5 seconds to spread the composite on the dentin surface. The pressure during the resin application to the dentin was somewhat less than 1.0 MPa because the tapered part of the iris supported some of the load. The assembly was let stand in air for 15 minutes, then immersed in distilled water at room temperature until tested 1–10 days later. The testing method was essentially the same as that described in Bowen R. L., "Adhesive Bonding of Various Materials to Hard Tooth Tissues. I. Method of Determining Bond Strength," 44 J. Dent. Res. 690–695 (1965); with the following exceptions: holes were drilled and tapped, and stainless steel screws were inserted into the extracted teeth to augment retention in the gypsum embedments. The flat part of the diaphragm contacting the dentin was covered by a poly(tetrafluoroethylene) film called Chemflour ® Pressure-Sensitive Tape, available from Chemplast, Inc., Wayne, N.J., to assure no tensile load transmission by way of this part; the total assembly was immersed and stored in water; the immersion time was usually 2–5 days rather than one day, and two-way tables were not used so that more variables could be screened. As reported in Bowen, R. L., "Adhesive Bonding of Various Materials to Hard Tooth Tissues. II. Bonding to Dentin Promoted by a Surface-Active Comonomer," 44 J. Dent. Res. 895–903 (1965), there seemed to be no correlation between bond strength and immersion time within this time range. The tensile load was applied by an Instron Tensile Tester, Model TTCL, available from Instron Eng. Corp., Quincy, Mass., at a rate of about 500 psi/min to determine adhesive bond strengths. The average tensile bond strengths are given in Table 1 ranked in descending order of average strengths. Although there was good reproducibility for a given treatment of the same tooth (assembly), there was considerably variation between teeth (assemblies). When the strengths were over 6.9 MPa (70 kg/cm²; 1000 psi), there were many incidences of teeth being pulled loose from the gypsum embedment, composite coming loose from the plunger part of the assembly, and some cases of fractured dentin; some specimens were sacrificed for scanning electron micrograph study. The average coefficient of variation was 25%.

Scanning electron micrographs showed dentinal tubules apparently unaffected by the treatment except close to the interface. There was no evidence of solids within the tubules except superficially. An edge view of quartz-filled composite remaining on the fracture surface after dissolving away dentin with 0.1N HCl for 33 minutes showed an absence of resin "tags" in areas where the dentinal tubules had been. There was also indication of a merging or blending of polymeric PMDM with the polymeric composite resin above and the altered dentin layer and the substrate dentin below. Below the altered dentin layer the dentinal tubules were empty.

(1,580–2,750 psi). The acid etch technique gave poor results (260–590 psi) with dentin and is not recommended for vital dentin.

Usually, the use of ferric oxalate/nitric acid, NTG-GMA, and PMDM did not produce any perceptible discoloration of the dentin, enamel, or composite. There were rare and sporadic instances of a black staining on

TABLE 1

Tensile Adhesive Strengths of a Composite Bonded to Treated Dentin Surfaces

| Dentin Surface Treatments | Average Adhesion | | | Standard Deviation + | Adhesion Range | No. of |
|---|---|---|---|---|---|---|
|  | (psi)* | (kg/cm²) | (MPa) | (MPa) | (MPa) | Measurement |
| Ferric oxalate, 6.8%# + NTG—GMA, 10% + PMDM§ | 2,180 | 153 | 15.0 | 4.8 | 7.2–20.6 | 8 |
| Ferric oxalate, 6.8%# + NPG, 10-11% + PMDM§ | 1,910 | 134 | 13.2 | 2.4 | 9.5–16.4 | 23 |
| Ferric oxalate, 6.8%# + NTG—GMA + PMDM§ | 1,900 | 134 | 13.1 | 2.3 | 10.2–18.2 | 11 |
| Ferric oxalate, 6.8%# + NPG—GMA + PMDM§ | 1,830 | 129 | 12.6 | 1.7 | 10.6–14.8 | 4 |
| Ferric oxalate, 6.8%# + NTG—GMA + 4-META | 1,790 | 125 | 12.3 | 2.4 | 10.8–14.5 | 6 |
| Ferric oxalate, 6.8%# + NTG—GMA + PMDM | 1,780 | 125 | 12.3 | 1.6 | 10.2–13.6 | 4 |
| Ferric oxalate, 6.8%# + NPG—GMA + 4-META | 1,680 | 118 | 11.6 | 3.7 | 5.5–16.5 | 9 |
| Ferric oxalate, 4%# + NTG—GMA + PMDM§ | 1,640 | 115 | 11.3 | 1.3 | 9.8–12.6 | 5 |
| Ferric oxalate, 4%# + NTG—GMA + PMDM | 1,610 | 113 | 11.1 | 2.0 | 9.4–13.3 | 3 |
| Ferric oxalate, #6.8% + NPG—GMA + 4-META | 1,310 | 92 | 9.0 | 1.2 | 8.2–9.9 | 2 |
| Ferric oxalate, 2%# + NTG—GMA + PMDM§ | 1,260 | 89 | 8.71 | 0.04 | 8.7–8.8 | 2 |
| Ferric oxalate, 6.8%# + 4-META + NPG—GMA | 1,130 | 80 | 7.8 | 1.8 | 5.4–8.9 | 4 |
| Water + NPG—GMA + 4-META | 900 | 63 | 6.2 | 3.8 | 3.5–8.9 | 2 |
| Ferric oxalate, 6.8%# + 4-META (no rinse) | 820 | 58 | 5.7 | 2.2 | 3.9–9.2 | 7 |
| Ferric oxalate, 6.8%# + NPG—GMA (no rinse) | 780 | 55 | 5.4 | 1.7 | 3.7–8.2 | 6 |
| Water + NTG—GMA + PMDM§ | 710 | 50 | 4.9 | 2.1 | 3.4–6.3 | 2 |
| Ferric oxalate, 6.8%# + 4-META + 4-META | 560 | 39 | 3.86 | 0.38 | 3.6–4.1 | 2 |
| Ferric oxalate, sat.**# + 4-META (no rinse) | 430 | 30 | 2.95 | 0.43 | 2.6–3.2 | 2 |
| Ferric oxalate, 6.8%# + NPG—GMA + NPG—GMA++ | 400 | 29 | 2.8 | 1.4 | 1.8–3.8 | 2 |
| Ferric oxalate, 6.8%# + 4-META (with rinse) | 390 | 28 | 2.7 | 1.4 | 1.7–3.7 | 2 |
| Water + 4-META (no rinse) | 340 | 23 | 2.3 | 1.1 | 1.6–3.1 | 2 |
| Water + 4-META (with rinse) | 260 | 18 | 1.79 | 0.41 | 1.5–2.1 | 10 |
| Ferric oxalate, 6.8%# + PMDM§ (no rinse) | 180 | 12 | 1.2 | 1.9 | 0.0–5.1 | 10 |
| Ferric oxalate, 6.8%# (only) | 160 | 11 | 1.10 | 0.83 | 0.48–1.72 | 2 |
| Water + acetone (control) | 8 | 0.6 | 0.06 | 0.09 | 0.00–0.20 | 5 |

To convert pounds of force per square inch, psi, to megapascals, MPa, multiply by 0.0068948; to convert MPa to kilograms of force per square centimeter, kg/cm², divide by 0.098044; to convert psi to kg/cm², divide by 14.22.
The standard deviation =

$$\frac{x_j^2 - nx^{-2}}{n-1}$$

In the tests reported in this table the NTG—GMA, PMDM, NPG—GMA, and 4-META were applied as 5-6% solutions in acetone, and the NPG was applied as a 10-11% solution in acetone, unless otherwise indicated.
§The isomer having a melting point of about 163° C.
The isomer with the melting point of about 153° C.
The ferric oxalate, the NPG—GMA, and the 4-META solutions were each applied for only 30 seconds.
**Saturated ferric oxalate solution; concentration estimated to be between 31 and 35%.
++Ten second acetone rinse after each application.
The ferric oxalate is believed to have contained a small amount of nitric acid.

The strongest bonds were obtained from treatment with aqueous ferric oxalate/nitric acid solution, NTG-GMA, acetone, and PMDM, in that order (Table 1); four of the 11 bonds treated with that combination each supported over one ton per square inch (over 2000 psi). The results suggest a synergistic interaction among the combinations and permutations of the ferric oxalate/nitric acid treatment, the application of the acetone solution of NTG-GMA, followed by an acetone solvent rinse, and then the application of the acetone solution of PMDM.

When the aqueous ferric oxalate (6.8%)/nitric acid, 5% NTG-GMA in acetone, acetone, and 5% PMDM in acetone preceded the application of the composite resin to enamel surfaces, the average tensile adhesive strength of the bonds was about the same (13.5 MPa; 138 kg/cm²; or 1960 psi; n=13) as that to dentin (13.1 MPa; 134 kg/cm²; or 1900 psi).

In later tests, using 6.8% aqueous ferric oxalate with nitric acid, 10% NTG-GMA in acetone, acetone, and 5% PMDM in acetone, bond strengths to enamel averaged 2,400 psi (s.d.=890; n=12) and to dentin averaged 2,020 psi (s.d.=430; n=23). An acid etch technique (30 ortho-phosphoric acid solution 60 seconds, wash 10 s, air jet 10 s) on enamel gave comparable values the dentin surface during prolonged immersion in water in the stainless steel assemblies wherein the teeth were embedded in gypsum (containing calcium sulfate). The gypsum surface was slowly dissolved away and the stainless steel equipment showed rusting or corrosion; it is conceivable that the discoloration was related in some way to those aspects of the equipment (and the formation of iron sulfide) rather than being an inherent potentiality of the materials interacting with dentin per se. This discoloration occurred occasionally both with the most preferred embodiment and with the embodiments less preferred as described below.

EXAMPLE 1g

In preliminary adhesion tests utilizing 6.8% aqueous ferric oxalate with nitric acid, 10% NTG-GMA in acetone, acetone, and then a crude solution of BTDA-HEMA in methanol (concentration not known), bond strengths averaged 1,960 psi (s.d.=510; n=5). In these tests, three samples were exposed to UV (an ultraviolet light source; Caulk ® Nuva-Lite ®, 40 secs.) before the composites were applied, and two were not exposed to UV. The former averaged 2,140 psi bond strength and the latter (without UV) averaged 1,670 psi. Both are strong bonds; but the ultraviolet light apparently improved the bond strengths, probably by increasing the degree of polymerization of the BTDA-HEMA (which is a benzophenone dimethacrylate) in the presence of NTG-GMA and/or triethylamine (tertiary amines).

EXAMPLE 1h

In additional adhesion tests utilizing 6.8% aqueous ferric oxalate with nitric acid, 10% NTG-GMA in acetone, acetone, and than a 6% acetone solution of PMDM, bond strengths to dentin averaged 2,180 psi (s.d.=700; n=8) (Table 1) and to enamel 2,290 (s.d.=120; n=3).

EXAMPLE 1i

In adhesion tests utilizing 6.8% aqueous ferric oxalate with nitric acid, 10 to 11% NPG in acetone, acetone, and then a 6% acetone solution of PMDM, bond strengths to dentin averaged 1,910 psi (s.d.=350; n=23) (Table 1) and to enamel 1,790 psi (s.d.=810; n=8).

EXAMPLE 1j

In additional tests designed to measure the effects of delaying the application of the freshly mixed composite to the treated dentin, no regular trend could be observed within the range of 0 to 30 minutes delay. In these tests, utilizing 6.8% aqueous ferric oxalate with nitric acid, 10% NPG in acetone, acetone, and then a 6% acetone solution of PMDM, bond strengths to dentin averaged 1,950 psi (s.d.=500; n=23) and to enamel 1,790 psi (s.d.=420; n=8).

EXAMPLE 1k

When two moles of the diglycidyl ether of bisphenol A were reacted with one mole of NPG, the derivative adduct gave significant but lower bond strengths. Namely, 6.8% ferric oxalate in water with nitric acid, 11% of this adduct in acetone, acetone, and then 6% PMDM in acetone yielded bond strengths to dentin of 1,060 psi (s.d.=320; n=8) and to enamel of 1,240 psi (s.d.=240; n=3).

EXAMPLE 1l

When absolute ethyl alcohol was used as the solvent for NPG and as the solvent to remove excess NPG from the tooth surface, intermediate average values and high variation in bond strengths was observed. 6.8% aqueous ferric oxalate with nitric acid, 10% NPG in ethanol, ethanol, and then 6% PMDM in acetone gave bond strengths of 960 psi (s.d.=910; n=7) to the dentin and 1,010 psi (s.d.=730; n=3) to the enamel of extracted human teeth.

EXAMPLE 1m

In a separate series of experiments, the general method of Examples 1a, 1c, 1e and 1f was employed, except that the concentration of nitric acid was varied from 0 to 10% in the first treatment solution as applied to dentin and enamel. (These solutions of variable nitric acid were prepared by rinsing a commercially available solution of 6.8% ferric oxalate with acetone to remove the nitric acid (a qualitative test confirmed removal of the acid), and then adding nitric acid to achieve the desired acid concentration.) Table 2 gives the pH's and osmolalities for the 6.8% ferric oxalate solutions with varying concentrations of nitric acid, and bond strengths in psi verus nitric acid concentration for the resulting bonds to dentin and enamel.

TABLE 2

| Nitric Acid Conc. (weight %) | pH | Osmolality (mOsm) | Bond Strength (psi) Dentin* | Bond Strength (psi) Enamel** |
|---|---|---|---|---|
| 0 | 1.8–1.9 | 430 | 960 | 500 |
| 0.068 | 1.63 | 452 | 1020 | 260 |
| 0.68 | 0.84–0.92 | 667 | 1030 | 1530 |
| 2.5 | 0.51 | 1358 | 1680 | 1740 |
| 5 | 0.26 | 2337 | 1270 | 1300 |
| 10 | −0.02 | >3000# | 1440 | 1180 |

*Average bond strength based on 15 or 16 measurements.
**Average bond strength based on 6 measurements.
Off scale.

As is apparent from Table 2, in this separate series of experiments all bond strengths seem to be shifted to a lower range, for reasons not yet elucidated. Nonetheless, it is apparent that on a relative basis, a nitric acid concentration of about 2.5% in the first treatment solution provides the strongest bonds for both dentin and enamel.

OTHER EMBODIMENTS OF THE INVENTION THAT ARE PREFERRED BUT NOT MOST PREFERRED

This aspect of the invention comprises other materials and methods for obtaining adhesion between composite materials and dentin and enamel that are clinically significant but which, according to test results, give bond strengths somewhat lower than those provided by the most preferred embodiments.

In the treatment of the surface of dentin or enamel with an aqueous solution of at least one acidic salt containing a polyvalent cation which preferably is capable of changing valence by unit steps, and which can bind to dentin or enamel surface sites, and at least one anion which preferably forms a relatively water-insoluble precipitate(s) with calcium, and which contains at least one carboxyl group and preferably two or more carboxyl groups, acidic salts other than ferric oxalate may be employed, with or without the addition of acid. An example of another acidic salt that can be used in the inventive procedure is ferric citrate in aqueous solution.

EXAMPLE 2

A 5% aqueous ferric citrate solution (pH 1.7; 138 mOsm) applied to dentin surfaces (in the same test procedure using NTG-GMA and PMDM as described previously, except with the ferric citrate solution substituting in place of the ferric oxalate/nitric acid solution) yielded an average adhesive bond strength from two measurements of 1440 psi. In one of these, there was cohesive failure of the dentin substrate surface at the time of bond fracture.

As an alternative to NTG-GMA in the practice of the inventive method, a solution of NPG-GMA can be used, yielding bond strengths that are comparable but not quite as high. Some comparisons are given in Table 1.

NPG-GMA is the addition reaction product of N-phenylglycine and glycidyl methacrylate and is of the formula:

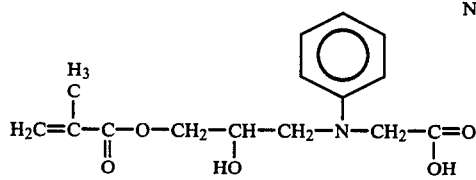

NPG—GMA

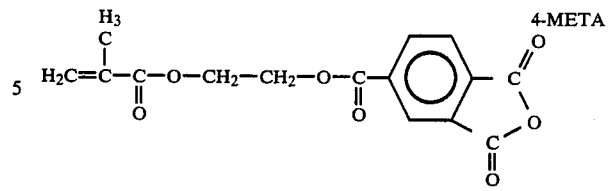

4-META

See Bowen, R. L., "Investigation of the Surfaces of Hard Tooth Tissues by a Surface Activity Test," in Phillips, R., & Ryge, G. (eds.): *Proceedings of the Workshop on Adhesive Restorative Dental Materials* 177–191 at Indiana University, Sept. 28–29, 1961, Spencer, Ind.: Owen Litho Service; and Bowen, R. L., U.S. Pat. No. 3,200,142. The method of synthesis of NPG-GMA is described in the literature: Bowen, R. L., "Development of an Adhesive Restorative Material," in *Adhesive Restorative Dental Materials II* 225–231, University of Virginia Workshop, Public Health Service Publication No. 1494, (Washington, D.C.: U.S. Government Printing Office, 1966); and Bowen, R. L., "Adhesive Bonding of Various Materials to Hard Tooth Tissues. II. Bonding to Dentin Promoted by a Surface-Active Comonomer," 44 *J. Dent. Res.* 895–902 (1965).

NPG, NPG-GMA and NTG-GMA can be purified by recrystallization from warmed, concentrated acetone solutions. Experience has established that for stability, NPG-GMA and NTG-GMA must be kept in contact with polymerization inhibitors at all times and protected from light and heat. Mixtures of acids and tertiary aromatic amines can initiate free radical polymerization of methacrylate monomers. Lal, et al., "New Polymerization Catalysts for Methyl Methacrylate," 24 *J. Polym. Sci.* 75–84 (1957); Uehara, "Polymerization of Methyl Methacrylate Initiated by a Combined Action of Trichoroacetic Acid and Dimethylaniline," 31 *Bull. Chem. Soc. Jap.* 685–687 (1958); Hrabak, et al., "The Initiation of Polymerization of Unsaturated Tertiary Amines with Carboxylic Acids," 182 *Macromol. Chem.* 1595–1603 (1981). With NPG-GMA or NTG-GMA, the acid, tertiary aromatic amine, and methacrylate groups are all together in the same molecule. Trace metallic ions might also contribute to their premature polymerization or autoxidation.

After excess NPG, NPG-GMA or NTG-GMA has been placed on the substrate surface and the solvent has evaporated, it tends to leave a somewhat chalky appearance due to recrystallization of the excess. This excess should be removed by the application of clean solvent which is physically removed after about 10 seconds.

NPG, NPG-GMA, and/or NTG-GMA can be used together as a mixture in a suitable solvent in any desired proportions.

In lieu of the PMDM and/or BTDA-HEMA discussed above, a solution of 4-META can be employed in the inventive method. The 4-META can be used in the same or different solvent(s).

4-META, which is somewhat less effective than PMDM and/or BTDA-HEMA, is 4-methacryloxyethyltrimellitic anhydride. The structural formula of 4-META, as reported in the literature (U.S. Pat. No. 4,148,988 issued Apr. 10, 1979, to Masuhara et al.) is:

EXAMPLE 3

4-META, or a mixture of 4-META and PMDM and/or BTDA-HEMA in any desired proportions may be applied to dentin or enamel preferably dissolved in a dry aprotic, volatile, water-miscible solvent (or mixture of solvents). A 5% solution of 4-META in anhydrous acetone is efficacious, but solutions from 0.1% to saturated might be used. Preferably, the excess solution of 4-META is not removed, and the surface of the dentin or enamel is blown, generally with air, to remove volatile solvents. Bond strengths utilizing 4-META together with other components of this invention are given in Table 1. The 4-META which was used in these experiments readily formed a clear 5% solution in acetone, and was kept in this form in an amber dropping bottle at room temperature.

In contrast to 4-META, PMDM can, if desired, be stored in and/or applied from protic solvents and/or mixtures of solvents containing water.

When a ferric oxalate treatment solution containing nitric acid was followed by NPG-GMA and then 4-META, the average bond strength was 11.6 MPa (118 kg/cm$^2$; 1680 psi); when the order of treatment with NPG-GMA and 4-META was reversed, the average was only 7.8 MPa (80 kg/cm$^2$; 1130 psi).

When the oxalate/nitric acid treatment was followed by only NPG-GMA or 4-META, the average was only 2.8 MPa (29 kg/cm$^2$; 400 psi) to 5.7 MPa (58 kg/cm$^2$; 820 psi). The oxalate/nitric acid without either was only about 1.1 MPa (11 kg/cm$^2$; 160 psi). Substituting water for the aqueous oxalate/nitric acid solution and acetone for the acetone solutions of the other compounds reduced the tensile bond strengths to practically zero.

Without the oxalate/nitric acid treatment, the combination of NPG-GMA plus 4-META (6.2 MPa; 63 kg/cm$^2$; or 900 psi) or of NTG-GMA plus PMDM (4.9 MPa; 50 kg/cm$^2$; or 710 psi) gave values about twice as high as did 4-META alone (about 2.1 MPa; 21 kg/cm$^2$; or 300 psi) or that (1.0–2.2 MPa; 10–22 kg/cm$^2$; or 150–320 psi) expected from NPG-GMA alone. Bowen, R. L., "Adhesive Bonding of Various Materials to Hard Tooth Tissues. II. Bonding to Dentin Promoted by a Surface-Active Comonomer," 44 *J. Dent. Res.* 895–902 (1965).

The application of the inventive combination of materials, preferably in the order first indicated, leads to a spontaneous polymerization in the absence of UV light or added heat. While literature has been found to show that oxalic acid can be induced to yield free radicals under the influence of UV (ultraviolet) or, in some cases, visible light (Palit, S. R. and Koner, R. S., "Permanganate-Oxalic Acid as a Redox Initiator in Aqueous Media," *J. Polymer Sci.* 609–615 (1962)), no literature has been found which explains the spontaneous polymerization of the inventive materials in the absence of UV light, blue light, or added heat. This spontaneous polymerization (with or without overlying resins of another kind) appears to be initiated at the surface because of the interaction of the components described herein. The bonding occurs by copolymerization of these materials with other polymerizable resins brought into contact with them.

EXAMPLE 4

In a darkroom with only minimal illumination from a darkroom safelight, two flat tooth surfaces obtained by sectioning extracted teeth were each treated with 6.8% aqueous ferric oxalate containing nitric acid, 10% NTG-GMA in acetone, acetone, and then a 5% acetone solution of PMDM; the treated surfaces were pressed together with finger pressure for three minutes; and then the specimen was immersed in water for three days. When removed from the water, the bond could be broken only with great difficulty. Scanning electron micrographs of the specimen showed that the PMDM layer had completely polymerized.

EXAMPLE 5

Adhesive bond strengths were tested wherein a comparison was made of specimens prepared in a darkroom with a safelight vs. those prepared in the light with a 20-second exposure to the bright white light of a commercial dental photoinitiation light source. The light was applied after the surface treatment, just before the application of the mixed composite resin. Although the specimens exposed to light had higher average strength, values of useful strength (1360 psi) resulted from those prepared in the dark. These latter strengths are higher than those of materials now commercially available for bonding composite materials to dentin.

Within the scope of this invention is the use of stabilizers, inhibitors, antioxidants, accelerators, promoters, initiators, UV and light-activated photoinitiators, (camphoroquinone, etc.) and other additives for the solutions of the soluble salts and acids, surface-active compounds (NPG, NTG, etc.), surface-active comonomers (NPG-GMA, NTG-GMA, etc.), and coupling agents (PMDM, etc.) described herein. Stabilizers or inhibitors, such as parabens (esters of p-hydroxybenzoic acid), and 2-methacryloxyethyl-p-hydroxybenzoate (Bowen, R. L., U.S. Pat. No. 3,635,889, Jan. 18, 1972), and other compounds to prevent microbial growth and for other reasons may optionally be added to the aqueous soluble salts. It may be desirable to add small amounts (such as 1 to 1,000 ppm) of antioxidants (e.g., butylated hydroxytoluene), polymerization inhibitors (e.g., the monomethyl ether of hydroquinone) and/or "stabilizers" (e.g., di-t-butyl sulfide) and other appropriate compounds, known to those skilled in the art, to provide adequate "shelf life" (storage stability) for the surface-active comonomers (e.g., NTG-GMA) and coupling agents (e.g., PMDM) or other solutions. Especially if polymerization inhibitors are used, which would tend to suppress the necessary polymerization of these (NTG-GMA, PMDM, etc.) during the adhesive bonding process, tertiary amines (e.g., N,N-dimethylaminoethyl methacrylate), peroxides (e.g., benzoyl peroxide), and photoinitiators (e.g., the methyl ether of benzoin and/or camphoroquinone) may be added to the surface-active comonomer and coupling agent formulations described herein. Also these polymerization initiators can be used in unfilled methacrylate resins ("bonding agents") described below.

An advantage of NPG is that polymerization inhibitors are not required for its storage stability. It or its solutions might benefit from the appropriate use of antioxidants, however.

Although Table 1 shows that treatment with ferric oxalate/nitric acid solution only did not yield strong bonding of composites to dentin surfaces (160 psi), it did prepare enamel surfaces for bonding if a "bonding agent," (an unfilled resin formulation containing polymerization initiators) was used:

EXAMPLE 6

Three enamel surfaces were treated with 6.8% aqueous ferric oxalate containing nitric acid for 60 seconds, washed with water 10 seconds, dried with compressed air 10 seconds; then a layer of mixed dental restorative bonding agent (Johnson and Johnson, East Windsor, N.J.) was applied before the composite was placed. The resulting average bond strength was 2,500 psi.

Lower, intermediate values would be expected for dentin surfaces treated with ferric oxalate/nitric acid solutions followed by such a "bonding agent."

As a further alternative, when coupling agent formulations (e.g., PMDM, BTDA-HEMA, 4-META etc.,) contain or are provided means for initiation of their polymerization (e.g., light, polymerization initiators) the use of the surface-active compound such as NTG or a surface-active comonomer such as NTG-GMA or NPG-GMA may be omitted, and the application of ferric oxalate may be followed by the application of these PMDM, BTDA-HEMA and/or 4-META formulations to obtain intermediate adhesive strengths.

DESCRIPTION OF OTHER ALTERNATIVE EMBODIMENTS

The foregoing disclosure describes certain embodiments of the invention that have been tested and proven of potential value in improving bonding specifically to dentin. The materials and methods were found also to bond resins to dental enamel, cementum, and other substrate surfaces. Other alternative embodiments are considered to fall within the scope of the invention because application of the inventive compounds and techniques in these alternative areas are believed to result in valuable adhesive bonding results. From the practice of the invention it is expected that many new and valuable applications in improved adhesive bonding of various monomers and polymers that harden by a free radical reaction to many industrial substrate surfaces can be obtained.

It is believed that bonding by this method may be improved especially (when utilizing resins, surface coatings, monomers, prepolymers, or plastics that harden by free radical reactions, and especially those bonded systems that are subsequently to be exposed to water or moisture) to industrial substrates which include or comprise various kinds of wood, wood products, cellulosic fibers, films, and materials having vicinal oxygen substituents on adjacent carbon atoms on accessible surfaces; metals, metal alloys, metal compounds, and metal composites having oxide or hydroxide surface groups containing or capable of binding the metallic cations listed below; glasses, microcrystalline glasses, ceramics, porcelains, natural and artificial minerals (both crystalline and amorphous), and inorganic solids having oxide or hydroxide surface groups; calcified, decalcified, and noncalcified substrates such as bone, ivory, horn, leather, and other collagenous, keratinous, and proteinaceous substances; and other solid materials, both natural and artificial, providing that they have vicinal or sufficient oxygen, nitrogen, or sulfur ligands to bind metallic cations on their surfaces.

Iron, steel, or alloy surfaces containing iron or other appropriate metals or metal oxides can be treated with a solution containing one or more "oligocarboxylic acids" to form the metal complex in situ (as might be the case, for example, when iron or steel surfaces are treated with oxalic acid or its salts to obtain a more corrosion resistant surface). Such a surface may or may not require the application of a soluble salt as listed below. In some cases, such a treated surface may then require only a surface-active compound or comonomer and a coupling agent as described herein.

In general, a substrate containing or capable of binding metallic ions is a candidate for enhancement of adhesive bonding by the method of the present invention.

In light of the spontaneous polymerization of the components of the invention in the absence of UV light, white light, or added heat, the inventive method would be expected to find numerous utilizations in industrial applications heretofore requiring exposure to light but in which the utilization of an adhesive system not requiring light would provide economic advantages. For example, the "anaerobic" adhesives would be expected to make valuable use of the new materials and methods. In addition to anaerobics, the acrylic, polyester, and vinyl acetate copolymer adhesives should find many new and improved bonding applications incorporating the preparation of the substrate surfaces described by this new method.

Also considered to be within the scope of the present invention is the use of soluble salts containing various elements forming polyvalent cations capable of changing valence by unit steps. These may include; e.g., Ti, V, Cr, Mn, Fe, Co, Ni, Cu, Tc, Re, Os, Ir, Hg, Ce, Sm, Eu, Yb, Pa, and U. One or more cations of these elements may be used (with or without cations of other elements) together with one or more of the dibasic or polybasic carboxylic acids ("oligocarboxylic acids") selected from the group including: dihydroxymaleic, diglycollic, oxalacetic, oxalic, malonic, succinic, glutaric, adipic, pimelic, suberic, azelaic, sebacic, malic, ethane-tetracarboxylic, phloionic, chloramalic, itaconic, citraconic, mesaconic, aconitic, citric, tartronic, chlorosuccinic, mesoxalic, tartaric, tricarballylic, acetone dicarboxylic, iso-citric, alpha-ketoglutaric, saccharic, mucic, talo-mucic, trihydroxyglutaric, phosphoglyceric, dimethyl malonic, N-phenyl-glycine-o-carboxylic, 1:2-cyclopropane-dicarboxylic, cyclopropane-1:1:2-tricarboxylic, cyclobutane-1:1-dicarboxylic, cyclobutane-1:2-dicarboxylic, cyclobutane-1:3-dicarboxylic, cyclobutane-1:1:3:3-tetracarboxylic, alpha-truxillic, beta-isotruxillic, 2:3-diphenyl-butane-1:1:4:4-tet-racarboxylic, cyclo-pentane-1:1-dicarboxylic, cyclopentane-1:2-dicarboxylic, apocamphoric, camphoric (d, l isomers), 2:5-dimethyl-cyclopentane-1:1-dicarboxylic, alpha,alpha'-di-sec.-butyl-glutaric, hexahydro-phthalic, hexahydro-terephthalic, hexahydro-isophthalic, beta-methyl-adipic, isopropyl-succinic, spiroheptane-carboxylic, alpha-tanacetogendicarboxylic, caronic, pinic, norpinic, methyl-succinic, trimethyl-succinic, 1:1-dimethyl-succinic, dehydrocamphoric, homocamphoric, apocamphoric, homoapocamphoric, methyl-nor-homocamphoric, iso-fenchocamphoric, alpha-hydroxy-iso-fenchocamphoric, alpha,alpha,alpha'alpha'-tetramethyl glutaric, 1:2-dimethyl succinic, 1:1-dimethyl-glutaric, dehydro-mucic (alpha,alpha'-furandicarboxylic), o-carboxyphenylthioglycollic, furazandicarboxylic, 4:5-triazole-dicarboxylic, meconic, 3:4:5:6-pyridazine-tetracarboxylic, uroxanic, 1:3:5-triazine-2:4:6-tricarboxylic, chelidonic, meta-hemipinic, cinchomeronic, alpha-carbo-cinchomeronic, hydrastic, 3:4:5-trimethoxy-1:2-phthalic, trimellitic, isophthalic, terephthalic, phthalic, and 4-methoxy-phthalic acid. Aqueous, or mixed solvent solutions of these are applied to the substrate surface to which bonding is desired.

Water, solvents, or mixtures of water with other solvents are used to prepare solutions of these cations and anions. These cations and anions can be used together as complex mixtures so as to form adequately soluble salt solutions for the first step of the present method. After exposure of the surface to such solutions, for a suitable length of time and at a suitable temperature, the excess solution and soluble reaction products can be washed away with water or the same or a different solvent mixture to obtain the desired structure and chemical composition of an altered surface. Not all combinations of cations and anions may be efficacious (e.g., aqueous solutions of titanium oxalate, titanium fluoride and titanium potassium oxalate yielded poor results when substituted for ferric oxalate/nitric acid), and an oxidizing or reducing agent may be advantageously employed in some cases to facilitate the unit change in valence state of the cation.

EXAMPLE 7

Two dentin surfaces were treated with an aqueous solution of pH 1.3 (703 mOsm) containing cupric cations and oxydiacetic (diglycollic) acid and sulfate anions; with an acetone solution of NTG-GMA; with an acetone solution of PMDM; then with a UV light. A composite resin bonded to these two surfaces with strengths of 1,480 and 1,920 psi, respectively; the dentin broken cohesively when the latter was tested.

Alternatively, the substrate surface may be acidified or treated with an acidic solution, e.g., with aqueous citric acid, in advance of or at the same time as application of the salt(s).

EXAMPLE 8

Dentin surfaces of 5 extracted teeth were treated with an isotonic citric acid solution; then with an aqueous solution containing cations of iron, copper, manganese, and cobalt, and anions of oxalic, citric, oxydiacetic, and tartaric acids, and ammonium ions. After rinsing with water and drying with an air stream, an acetone solution of NTG-GMA was then applied to the pretreated surfaces followed by an acetone solution of PMDM. A UV light was shined on the surfaces, and mixed composite resin was placed on each in the usual way. After immersion in water for one week the tensile adhesive bond strengths were found to average 2,400 psi. In one of these, which broke at 3,230 psi, a piece of dentin was pulled out of the tooth surface when the bond broke.

Other acids, e.g., phosphoric acid, hydrochloric acid, sulfuric acid and others, may logically be employed in treating the substrate surface before application of the surface active compound.

After the altered surface is optionally dried, it is then exposed to a solution of one or more surface-active compounds each of which contain at least one carboxyl and aromatic amino group. For example, NTG may be used, as such, in the present invention as a surface-active compound in place of or admixed with NPG, NPG-GMA, NTG-GMA, or other surface-active compound(s). The surface-active compounds are preferably of the following structure:

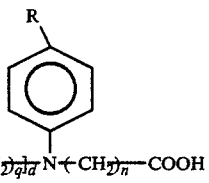

H$\text{-(CH}_2\text{)}_r$COO$\text{-(CH}_2\text{)}_p$$\text{-(CHOH)}_m$$\text{-(CH}_2\text{)}_q]_d$N$\text{-(CH}_2\text{)}_n$—COOH where:
- d=0 or 1, preferably 0;
- m=0 to 6, preferably 0;
- n=1 to 10, preferably 1 or 2;
- p=0 to 12, preferably 0;
- q=0 to 2, preferably 0;
- r=0 to 10, preferably 0 or 1;
- m+p+q=0 to 20; preferably 0;
- R may be $\text{-(O)}_f\text{(CH}_2\text{)}_t$H; straight or branched aliphatic groups, with f=0 or 1, preferably 0; and with t=0 to 12, preferably 1 or 2;

and/or
- R may be $\text{-(O)}_f\text{(CH}_2\text{)}_t$COOH, with t=0 to 12, preferably 1 or 2; and with f=0 or 1, preferably 0;

and/or
- R may be $\text{-(O)}_f\text{(CH}_2\text{)}_d$O—H, with d=1 to 12, preferably 2, and with f=0 or 1, preferably 0;

and/or
- R may be F, Cl, Br, I;

and
- the number of R groups per molecule is 0 to 5, preferably 1; and these R groups may be in the para, meta, or ortho positions relative to the nitrogen, preferably in the para and/or meta position.

Alternatively, after the pretreated surface is optionally dried, it is then exposed to a solution of one or more surface-active comonomer compounds each of which contain at least one of each of the following groups: carboxyl, tertiary amino, and carbon-to-carbon double bond capable of free radical polymerization. The surface-active comonomer compounds are preferably of the following structure:

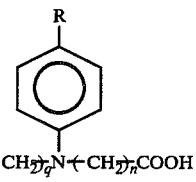

H$\text{-(CH}_2\text{)}_r$C(=CH$_2$)—COO$\text{-(CH}_2\text{)}_p$$\text{-(CHOH)}_m$$\text{-(CH}_2\text{)}_q$N$\text{-(CH}_2\text{)}_n$COOH where:
- m=0 to 6, preferably 1 or 2;
- n=1 to 10, preferably 1 or 2;
- p=0 to 12, preferably 1;
- q=0 to 2, preferably 1;
- r=0 or 1, preferably 1;
- m+p+q=2 to 20, preferably 3;
- R may be $\text{-(O)}_f\text{(CH}_2\text{)}_t$H; straight or branched aliphatic groups, with f=0 or 1, preferably 0; and with t=0 to 12, preferably 1 or 2;

and/or
- R may be $\text{-(O)}_f\text{(CH}_2\text{)}_t$COOH, with t=0 to 12, preferably 1 or 2; and with f=0 or 1, preferably 0;

and/or
- R may be $\text{-(O)}_f\text{(CH}_2\text{)}_d$O—H, with d=1 to 12, preferably 2, and with f=0 or 1, preferably 0;

and/or
- R may be F, Cl, Br, I;

and
- the number of R groups per molecule is 0 to 5, preferably 1; and these R groups may be in the para, meta, or ortho positions relative to the nitrogen, preferably in the para and/or meta position.

EXAMPLE 9

A surface-active comonomer which will be denominated NPCG-GMA (wherein R in the preceding formula is Cl) was prepared from p-chloroanaline, monochloroacetic acid, and glycidyl methacrylate; this compound (m.p.=117°–122° C.), as a 10% solution in acetone, was placed on two dentin surfaces after the surfaces had been treated with ferric oxalate solution (6.8%) containing nitric acid. Then, a 5% PMDM solution in acetone was applied, and the treated surfaces were exposed to UV for 40 seconds before the composite was applied. In the testing of adhesion (as described above), one bond broke at 1,640 psi. In the other case, the composite came loose from the assembly at 1,520 psi (the adhesive bond did not break).

These compounds, described herein as "surface-active compounds" or "surface-active comonomers", can be applied in various forms, including solutions in solvents such as acetone, methylethyl ketone, diethyl ketone, cyclohexanone, and other ketonic solvents; methanol, ethanol, propanol, butanol, and higher linear or branched hydroxy-containing solvents; ethyl acetate, vinyl acetate, methyl methacrylate, and other esters; various ethers, chlorinated solvents, saturated and unsaturated hydrocarbons; and mixtures of the foregoing, as well as other solvents. However, some solvents appear to give higher bond strengths than do others, as illustrated in the following examples:

EXAMPLE 10

In one set of adhesion tests, utilizing the preferred combination of ferric oxalate with nitric acid, NTG-GMA, and PMDM; NTG-GMA was dissolved in isopropyl alcohol (2-propanol). The matched bond strengths using acetone as a solvent for NTG-GMA averaged 1930 psi compared with only 860 psi for those in which 2-propanol was used as a solvent for NTG-GMA.

EXAMPLE 11

A solvent mixture considered to be within the scope of this invention is a mixture of ethanol and hexane. A mixture with about 42 vol % ethanol and 58 vol % hexane is predicted to have a solubility parameter of approximately 9.6 (which is about that of acetone and, therefore, believed capable of dissolving NPG, NPG-GMA, NTG-GMA, PMDM and similar compounds). These solvents form a terniary azeotrope with water boiling at about 56° C. (the boiling point of acetone). The ethanol-hexane azeotrope (18 vol % ethanol) boils at about 59° C. Both ethanol and hexane form azeotropes with water.

EXAMPLE 12

Another potential solvent for the surface-active compounds (NPG, NTG-GMA, NPG-GMA, etc.) and/or for the coupling agents (PMDM, etc.) falling within the scope of this invention is mixtures of methyl methacrylate monomer and ethanol. A mixture with 84% methyl methacrylate ("MMA") and 16% by weight of ethanol would be expected to dissolve these solutes. Both ethanol and MMA form azeotropes with water. However, adhesion tests using these solvents gave mixed results. Tests using 6.8% ferric oxalate with nitric acid in water, 5.2% NTG-GMA in a solvent mixture of 84% methyl methacrylate plus 16% absolute ethanol (w/w), the above solvent mixture to remove the excess NTG-GMA, then 5% PMDM in acetone gave adhesive strengths of 1,800 psi (s.d.=640; n=5) with dentin and 2,960 psi (s.d.=660; n=3) with enamel. When this MMA-ethanol mixture was used for both NTG-GMA and PMDM the bond strengths were 580 psi (s.d.=470; n=7) with dentin and 2,600 psi (s.d.=550; n=3) with enamel. When the NTG-GMA was in acetone and the PMDM was in this solvent mixture, the bond strengths were 690 psi (s.d.=310; n=7) to dentin and 3,170 psi (s.d.=590; n=3) to enamel.

EXAMPLE 13

Another potential solvent is a mixture of ethanol plus ethyl acetate; 84% ethyl acetate with 16% ethanol should serve as a solvent for the surface-active compounds and coupling agents of this invention. These solvents also form azeotropes with one another, and together and individually, with water.

The selection of additional solvents other than those tested and described in The Most Preferred Embodiments herein may be made by one of ordinary skill in the art.

The purpose of the application of the clean solvent, such as acetone or other solvents, after the solvent solution of the surface-active compound or comonomer has been applied to the substrate surface(s), is considered to be primarily that of removal of excess surface-active compound or comonomer that has not been chemically or physically bound to the substrate surface(s). The best results have been obtained when sufficiently high concentrations of the surface-active compound or comonomer are presented to the substrate so that maximum adsorption or chemisorption can occur within the time allowed for the application. When a volatile solvent like acetone is used, the surface-active compound or comonomer solution on the surface rapidly becomes increasingly concentrated until it reaches saturation; thereafter, crystals of the compound or comonomer can form and be deposited on the surface. These crystals can have the effect of weak boundary layer material that could lessen the strength of the bonds. Therefore, in the most preferred method, a clean solvent is used to remove this unbound surface-active compound or comonomer. With the use of other solvents, and/or under industrial or other conditions of application, it may not be necessary to use clean solvent, but rather to use an appropriate concentration of solvent and to remove the solution in such a way that the optimum amount of surface-active compound or comonomer is adsorbed on the surface without the need for a separate rinse step in the procedure. Therefore, the procedure as performed by one skilled in the art would provide conditions for the optimum (e.g., maximum) adsorption and chemisorption of the surface-active compound or monomeric surface-active comonomer (such as NTG-GMA), with little or no deposition of crystals or other excess of this material above that which is adsorbed or chemisorbed by the substrate.

The next step in the preparation of the surface for bonding with free radical polymerizing resins involves the application of one or more coupling agents optionally in the form of a solution in one or a mixture of solvents.

One characteristic of the coupling agent (PMDM, etc.) employed in the inventive method is that it has one or more aromatic groups which are electron-deficient due to electron withdrawing substituents. Electron-poor rings can interact attractively with, and possibly with electron-transfer from, electron-rich rings (such as those contained in the surface-active compounds such as NPG and surface-active comonomers such as NPG-GMA, NTG-GMA, etc.) which have electron-donating substituents.

Another advantageous characteristic of coupling agents used in the invention is their possession of carboxylic groups or anhydride groups (which can form carboxyl groups on hydrolysis and/or react with substrate groups). Carboxyl groups probably contribute to complex formation, salt-bond formation, hydrogen bonding, and to other polar interactions with substrate cations and associated groups.

The coupling agents must also have at least one and preferably two or more polymerizable groups per molecule so that the resulting polymer immediately above the interface will become cross-linked; the polymer should become strong, hard, and insoluble. A mixture can be used, some monomers having one and others two or more polymerizable groups.

With these considerations in mind, the following gives a description of compounds considered in most cases to be suitable for use as coupling agents and within the scope of this invention:

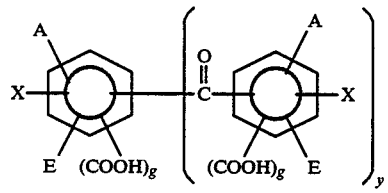

where:
g=0 to 7, preferably 2;
E is a polymerizable moiety:
$-(COO-(CH(CH_2)_jH)_q(CHOH)_m(CH_2-)_pOCO-(C-(CH_2)_rH)=CH_2$; wherein
r=0 or 1, preferably 1;
p=0 to 12, preferably 1;
m=0 to 6, preferably 0;
q=0 to 2, preferably 1;
j=0 or 1, preferably 0;
p+m+q=2 to 20, preferably 2;
the number of E groups per molecule is 1 to 8, preferably 2;
A is an anhydride group —OCOCO— (attached to vicinal ring carbon atoms); the number of A groups per molecule is 0 to 1, preferably 0 or 1;
X is a halide group; and the number of X groups per molecule is 0 to 8, preferably 0; and
y is 0 to 1, preferably 0.

It should be understood that the foregoing disclosure emphasizes certain specific embodiments of the invention and that all modifications or alternatives equivalent thereto are within the spirit or scope of the invention as set forth in the appended claims.

What is claimed is:

1. A method for preparing the surface of dentin or enamel for adhesion of composite materials or resins, which method comprises:
   (a) contacting with the surface of the dentin or enamel an aqueous solution or solutions comprising (1) at least on acidic salt containing a polyvalent cation which is capable of changing valence by unit steps and which can bind to dentin or enamel surface sites, and at least one anion which forms a relatively water-insoluble precipitate or precipitates with calcium and which contains at least one carboxyl group; and (2) acid;
   (b) contacting with the surface of the dentin or enamel a solution comprising at least one compound selected from the group consisting of (1) N-phenylglycine, (2) the adduct of N(p-tolyl)gylcine and glycidyl methacrylate, and (3) the addition reaction product of N-phenylglycine and glycidyl methacrylate in a solvent; and
   (c) contacting with the surface of the dentin or enamel a solution comprising at least one compound selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, and (3) 4-methacryloxyethyltrimellitic anhydride.

2. A method as in claim 1 wherein the concentration of the acidic salt solution is from about 0.1% to a saturated solution.

3. A method as in claim 1 wherein the cation of the acidic salt forms a relatively insoluble phosphate.

4. A method as in claim 1 wherein the acidic salt is ferric oxalate.

5. A method as in claim 1 wherein the acidic salt is ferric citrate.

6. A method as in claim 1 wherein the acid is nitric acid.

7. A method as in claim 1 wherein the concentration of the solution comprising at least one compound selected from the group consisting of (1) N-phenylglycine, (2) the adduct of N(p-tolyl)gylcine and glycidyl methacrylate, and (3) the addition reaction product of N-phenylglycine and glycidyl methacrylate in a solvent is from about 0.1% to a saturated solution.

8. A method as in claim 1 wherein the concentration of the solution of at least one compound selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, and (3) 4-methacryloxyethyltrimellitic anhydride is from about 0.1% to a saturated solution.

9. A method as in claim 1 wherein the solvent for the solution of subpart (b) is acetone.

10. A method as in claim 1 wherein the solvent for the solution of subpart (c) is acetone.

11. A method as in claim 1 wherein the steps (a), (b) and (c) are performed in that order.

12. A method for preparing the surface of dentin or enamel for adhesion of composite materials or resins, which method comprises:
    (a) contacting the surface of the dentin or enamel with an aqueous solution comprising ferric oxalate and nitric acid;
    (b) washing and then drying the surface of the dentin or enamel;
    (c) contacting the surface of the dentin or enamel with a first acetone solution comprising at least one compound selected form the group consisting of (1) N-phenylglycine, (2) the adduct of N(p-tolyl)glycine and glycidyl methacrylate, and (3) the addition reaction product of N-phenylglycine and glycidyl methacrylate in acetone;
    (d) removing any excess of the first acetone solution and rinsing the surface of the dentin or enamel with acetone, removing any excess acetone and drying the surface;
    (e) contacting the surface of the dentin or enamel with a second acetone solution comprising at least one compound selected from the group consisting of (1) the addition reaction product of pyromellitic acid dianhydride and 2-hydroxyethyl methacrylate and (2) the addition reaction product of 3,3',4,4'-benzophenonetetracarboxylic dianhydride and 2-hydroxyethyl methacrylate.

13. A method as in claim 12 wherein the concentration of ferric oxalate in the aqueous solution comprising ferric oxalate and nitric acid is about 6.8% of the hexahydrate.

14. A method as in claim 12 wherein the concentration of nitric acid in the aqueous solution comprising ferric oxalate and nitric acid is between 0 and 50%.

15. A method as in claim 12 wherein the concentration of nitric acid in the aqueous solution comprising ferric oxalate and nitric acid is between about 0.068 and about 10%.

16. A method as in claim 12 wherein the concentration of nitric acid in the aqueous solution comprising ferric oxalate and nitric acid is about 0.68%.

17. A method as in claim 12 wherein the concentration of nitric acid in the aqueous solution comprising ferric oxalate and nitric acid is about 2.5%.

18. A method as in claim 12 wherein the concentration of ferric oxalate in the aqueous solution comprising ferric oxalate and nitric acid is about 4% of the hexahydrate.

19. A method as in claim 12 wherein the washing medium is water.

20. A method as in claim 12 wherein the compound in the first acetone solution is N-phenylglycine.

21. A method as in claim 12 wherein the concentration of the compound in the first acetone solution is about 10% of the N-phenylglycine in acetone.

22. A method as in claim 12 wherein the compound in the second acetone solution is the addition reaction product of pyromellitic acid dianhydride and 2-hydroxyethyl methacrylate.

23. A method as in claim 22 wherein the concentration of the compound in the second acetone solution is about 5%.

24. A method for preparing the surface of dentin, enamel or industrial substrates for adhesion of composite materials or resins, which method comprises:
    (a) contacting with the surface of the dentin, enamel or industrial substrate an aqueous solution or solutions comprising (1) at least one acidic salt containing a polyvalent cation which is capable of changing valence by unit steps and which can bind to dentin, enamel, or industrial substrate surface sites, and at least one anion which forms a relatively water-insoluble precipitate or precipitates with cations of the substrate surface and which contains at least one carboxyl group; and (2) acid;

(b) contacting with the surface of the dentin, enamel or industrial substrate a solution comprising a solvent and a surface-active compound of the formula:

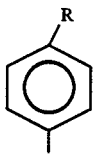

H$\{$(CH$_2$)$_r$COO$\}_f$(CH$_2$)$_p$(COOH)$_m$(CH$_2$)$_q$]$_d$N(CH$_2$)$_n$—COOH where:
- $d = 0$ or $1$;
- $m = 0$ to $6$;
- $n = 1$ to $10$;
- $p = 0$ to $12$;
- $q = 0$ to $12$;
- $r = 0$ to $10$;
- $m + p + q = 0$ to $20$;
- R is selected from the following groups:
  (a) $-(O)_f(CH_2)_tH$ straight or branched aliphatic groups, with $f = 0$ or $1$, and with $t = 0$ to $12$;
  (b) $-(O)_f(CH_2)_tCOOH$, with $t = 0$ to $12$, and with $f = 0$ or $1$;
  (c) $-(O)_f(CH_2)_dO-H$, with $d = 1$ to $12$; and with $f = 0$ or $1$; and
  (d) F, Cl, Br and I;

and the number of R groups per molecule is 0 to 5, and these R groups are in the para meta, or ortho positions relative to the nitrogen;

(c) contacting with the surface of the dentin, enamel, or industrial substrate a solution comprising at least one coupling agent of the formula:

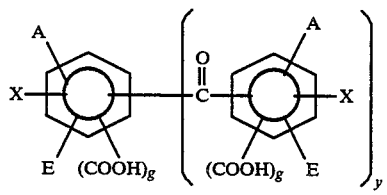

where:
- $g = 0$ to $7$;
- E is a polymerizable moiety:
  $-(COO-(CH(CH_2)_jH)_q(CHOH)_m(CH_2-)_pOCO-C-(CH_2)_rH)=CH_2$; wherein
- $r = 0$ or $1$;
- $p = 0$ to $12$;
- $m = 0$ to $6$;
- $q = 0$ to $2$;
- $j = 0$ or $1$;
- $p + m + q = 2$ to $20$;

the number of E groups per molecule is 1 to 8;

A is an anhydride group —OCOCO— (attached to vicinal ring carbon atoms); the number of A groups per molecule is 0 to 1;

X is a halide group; and the number of X groups per molecule is 0 to 8;

and $y$ is 0 to 1.

25. An article of manufacture comprising in combination:
(a) a first closed compartment containing a composition comprising (1) at least one acidic salt containing a polyvalent cation which is capable of changing valence by unit steps and which can bind to dentin or enamel surface sites, and at least one anion which forms a relatively water-insoluble precipitate or precipitates with calcium and which contains at least one carboxyl group; and (2) acid;
(b) a second closed compartment containing a composition comprising at least one compound selected from the group consisting of (1) N-phenylglycine, (2) the adduct of N(p-tolyl)glycine and glycidyl methacrylate, and (3) the addition reaction product of N-phenylglycine and glycidyl methacrylate; and
(c) a third closed compartment containing a composition comprising at least one compound selected from the group consisting of (1) the addition reaction product of pyromellitic acid dianhydride and 2-hydroxyethyl methacrylate, (2) the addition reaction product of 3,3′,4,4′-benzophenonetetracarboxylic dianhydride and 2-hydroxyethyl methacrylate, and (3) 4-methacryloxyethyltrimellitic anhydride.

26. An article of manufacture as in claim 25 wherein the first, second and third closed compartments are impervious to ultraviolet and visible light.

27. An article of manufacture as in claim 25 wherein the contents of the first, second and third closed compartments are in solutions.

28. An article of manufacture comprising in combination:
(a) a first closed compartment, which is impervious to ultraviolet and visible light, containing a composition comprising ferric oxalate and nitric acid;
(b) a second closed compartment, which is impervious to ultraviolet and visible light, containing a composition comprising N-phenylglycine; and
(c) a third closed compartment, which is impervious to ultraviolet and visible light, containing a composition comprising the addition reaction product of pyromellitic acid dianhydride and 2-hydroxyethyl methacrylate.

29. A structure comprising a composite material or resin bonded to a dentin or enamel surface which has been prepared by the method of claim 1.

30. A structure comprising a composite material or resin bonded to a dentin or enamel surface which has been prepared by the method of claim 4.

31. A structure comprising a composite material or resin bonded to a dentin or enamel surface which has been prepared by the method of claim 6.

32. A structure comprising a composite material or resin bonded to a dentin or enamel surface which has been prepared by the method of claim 12.

* * * * *